(12) United States Patent
Tajima (10) Patent No.: US 7,157,047 B2
(45) Date of Patent: Jan. 2, 2007

(54) DEVICE FOR CONTAINING, REACTING AND MEASURING, AND METHOD OF CONTAINING, REACTING AND MEASURING

(75) Inventor: Hideji Tajima, Inagi (JP)

(73) Assignee: PSS Bio Instruments, Inc., Livermore, CA (US)

( * ) Notice: Subject to any disclaimer, the term of this patent is extended or adjusted under 35 U.S.C. 154(b) by 0 days.

(21) Appl. No.: 09/909,186

(22) Filed: Jul. 19, 2001

(65) Prior Publication Data

US 2002/0110817 A1    Aug. 15, 2002

(30) Foreign Application Priority Data

Feb. 9, 2001   (JP)   ............................. 2001-034556

(51) Int. Cl.
*G01N 21/64* (2006.01)
(52) U.S. Cl. .......................... 422/57; 422/56; 422/58; 422/59; 422/82.08; 435/287.9; 435/288.7
(58) Field of Classification Search ................ 422/50, 422/55, 56, 58, 68.1, 82.05
See application file for complete search history.

(56) References Cited

U.S. PATENT DOCUMENTS

| | | | |
|---|---|---|---|
| 4,031,399 A * | 6/1977 | Klein et al. .............. 250/461.2 |
| 4,447,546 A * | 5/1984 | Hirschfeld .................. 436/527 |
| 4,551,435 A * | 11/1985 | Liberti et al. ............... 436/541 |
| 4,844,869 A * | 7/1989 | Glass ...................... 422/82.08 |
| 5,082,630 A * | 1/1992 | Partin et al. ................. 422/83 |
| 5,525,466 A * | 6/1996 | Slovacek et al. .............. 435/6 |
| 6,057,100 A * | 5/2000 | Heyneker ...................... 435/6 |
| 6,251,688 B1 * | 6/2001 | Erb et al. ................... 436/518 |
| 6,310,352 B1 * | 10/2001 | Gross et al. ........... 250/370.11 |
| 6,482,593 B1 * | 11/2002 | Walt et al. ..................... 435/6 |

\* cited by examiner

*Primary Examiner*—Jill Warden
*Assistant Examiner*—Paul Hyun
(74) *Attorney, Agent, or Firm*—Haynes and Boone, LLP (57) ABSTRACT

The invention relates to a device for containing, reacting and measuring, and a method of containing, reacting and measuring, and provides a device for containing, reacting and measuring, and a method of containing, reacting and measuring which is also able to effectively and quickly perform the reaction processing, measuring and identification. The invention comprises; a transparent container section having a liquid inlet/outlet and which is able to contain a base member with various substances for detection having predetermined chemical structures fixed at respective fixed positions which are arranged in a predetermined condition, and with each of the chemical structures associated with each of the fixed positions, a drawing and discharging section which is able to draw and discharge the liquid into and from the container section via the inlet/outlet, and a measuring device which is able to receive light from the contained base member, external to the container section and in a condition associated with the fixed position.

20 Claims, 6 Drawing Sheets

DEVICE FOR CONTAINING, REACTING AND MEASURING, AND METHOD OF CONTAINING, REACTING AND MEASURING

The referenced application claims benefit to Japanese Patent Application No. 2001-034556, filed Feb. 9, 2001.

TECHNICAL FIELD

The present invention relates to a device for containing, reacting and measuring, and a method of containing, reacting and measuring. The invention relates to all manner of fields which require the handling of low molecular weight organisms and biopolymers such as genes, immune systems, amino acids, proteins and sugars, including for example the fields of engineering, agricultural science incorporating foodstuffs, agricultural production and seafood processing, pharmaceuticals, the medical field incorporating hygiene, health, immunity, disease and genetics, and scientific fields such as chemistry and biology.

In particular, the present invention relates to a device for containing, reacting and measuring and a method of containing, reacting and measuring which is suitable for the analysis of genes including mutational analysis, polymorphic analysis, mapping, base sequence analysis, and mechanism analysis.

BACKGROUND ART

Currently, when determining gene base sequences a DNA chip is used.

This DNA chip is a flat sheet comprising a semiconductor film or a slide glass on to which is spotted a minute quantity of suspensions of a large number of different, known oligonucleotides, with the oligonucleotides fixed in an array pattern sequence. The DNA chip is made by using a pipette apparatus in order to form a plurality of oligonucleotides on the restricted surface thereof, minute quantities of oligonucleotide suspensions being dispensed spot by spot on to the surface while leaving a predetermined separation between adjacent spots to prevent mixing. By using such a DNA chip, various assay or analysis related to genes is performed.

For example, in determining the base sequence of an unknown target gene, conventionally the user pours a liquid with the target genetic material suspended therein and which is labeled with a luminescent material, onto the DNA chip. Then after leaving for a fixed reaction time, the surplus suspension is removed by washing. Subsequently, the luminescence from the DNA chip is detected to thereby determine the base sequence from the position where the luminescence is detected.

However, in order to manufacture the DNA chip, with the arrangement of a large number of different oligonucleotides at a high density in a plane on a restricted region, not only is there the likelihood of cross-contamination occurring due to these becoming close to each other, but also the oligonucleotides at each of the fixed positions becomes an even smaller amount. In particular, if the oligonucleotides at each of the fixed positions becomes a small amount, determining the luminescence position is susceptible to error so that there is a problem with accuracy. Furthermore, due to miniaturization, there is a problem in that the encounter characteristics or reactivity of the target substance is reduced, so that processing takes time.

Moreover, since the sample is arranged in a plane, then with higher densities, the handling and automation thereof is even more difficult. Consequently, the manufacture of the DNA chip requires a considerable amount of effort and time, resulting in high cost. In particular, in performing analysis, assay or determination of the structure of large amounts of unknown target substances which contain base sequences, the analysis, assay etc. of a large amount of DNA chips is necessary. Therefore, the present applicant in order to solve this problem has disclosed in patent applications (Unpublished Patent Application Nos. 2000-7763, 2000-37273, 2000-77144, not yet published at the time of this application), an integrated support which has one, or two or more long slender base members of for example filaments, fibers, tapes, or rods, and a variety of substances for detection of predetermined chemical structures which are lined up and fixed along the longitudinal direction of the base member, the base member being rolled, laminated or arranged in a line, so that the fixed locations of each type of substance for detection is associated with the chemical structure thereof.

However, even though the manufacture of such an integrated carrier is simplified and the cost reduced, there is a problem in that if reaction, measuring and identification using such an integrated carrier cannot also be performed efficiently and quickly, the advantage of this integrated carrier cannot be sufficiently realized.

Therefore, the present invention aims to resolve the problems outlined above, with a first object of providing a device for containing, reacting and measuring and a method of containing, reacting and measuring, which is able to effectively and quickly perform reaction, measuring and identification not only for the aforementioned carrier but also for the DNA chip.

A second object of the present invention is to provide a device for containing, reacting and measuring and a method of containing, reacting and measuring, which can consistently and automatically perform reaction, measuring, and identification of a target substance.

A third object of the present invention is to provide an easily operated device for containing, reacting and measuring and a method of containing, reacting and measuring which can perform reaction, measuring, and identification using a minute amount of liquid in which is suspended a labeled target substance.

A fourth object of the present invention is to provide a highly reliable device for containing, reacting and measuring, and a method of containing, reacting and measuring which can perform accurate identification of a target substance.

A fifth object of the present invention is to provide an integrated carrier where reaction, measuring and identification is further simplified.

DISCLOSURE OF THE INVENTION

In order to solve the above technical problems, a first aspect of the invention is an integrated carrier having; a base member of a long and slender shape such as a filament, a braid, or tape, with various substances for detection having predetermined chemical structures fixed thereto so as to be lined up along a longitudinal direction thereof with each of the chemical structures associated with their fixed positions, and a carrier with the base member rolled therearound with each of the fixed positions exposed outwards.

Here substance for detection is an already known substance to be detected in order to determine a structure of a target substance, or to conduct various assays or analyses, and includes genetic material such as oligonucleotides, biopolymers such as proteins, amino acids and sugars, microorganisms such as low molecular weight organisms or bacteria and viruses, and living systems such as cells.

Genetic material includes nucleic acid (polynucleotide) and its decomposition products oligonucleotides, nucleotides and so forth. Here, base member is formed from a flexible material or a non flexible material. This material may be for example an organic material such as polyethylene, polystyrene, polypropylene, urethane, an inorganic material such as glass fiber, ceramics, metal, or a material where organic and inorganic materials are combined such as where fine ceramics particles are spread all over a film or tape of an organic material. Furthermore the base member, may be formed, at least in each fixed position, from various types of porous material, foammaterial, fibrous material, or irregular surface material.

"Associating" preferably involves for example relating to positions on a layer forming face (integrated face) constituting a layered structure produced by rolling the base member. "The base member is rolled on the surface so that the fixed positions are exposed to the outside", is so that measurement can be made from outside of the container section. Consequently, a normal situation where the base member is rolled on the carrier in only one layer in for example a cylindrical shape is preferably.

Furthermore, the fixed positions are provided at the layer forming face side of the base member. "Chemical structure" for example in the case where the substance for detection is a genetic material, is a base sequence. Regarding "rolled base member", preferably the base member is united and held by for example positioning the edges of the base member in a space provided on the carrier and fixing by frictional force.

Furthermore, regarding the integrated member, when this is contained in a container section described later, preferably this has a construction such that a space is formed with the inner wall of the container section so that liquid can flow smoothly therethrough. As a result, when the liquid is drawn, the liquid can be reliably contacted with the substance for detection, and when the liquid is discharged, the liquid can pass smoothly between the integrated carrier and the inner wall, leaving no residual liquid.

Such a construction is preferably realized by providing on the carrier (for example cylindrical or prismatic shape) about which the base member is rolled, a protective portion for preventing contact of the base member with the inner wall of the container (also including a later described container section) for containing the integrated carrier. The protective portion is preferably one where a protruding portion having a height exceeding the thickness of the rolled base member and with a tip thereof for contact with the container inner wall, is provided for example on a suitable part (for example opposite rim portions, opposite end portions etc.) of the carrier (for example cylindrical or prismatic shape), protruding from the surface of the carrier (for example in the radial direction).

Moreover, preferably the contact point of the protective portion with the container inner wall is formed so as to have a minimal area. This is because if the area of the contact point is large, the amount of residual liquid is likely to increase. The shape of the protective portion is formed so that flow of liquid inside the container portion does not become impossible due to the presence of the protective portion. This situation is prevented for example by providing cutouts in an annularly formed protruding portion, or by providing a pin-like protruding portion. By means of this protective portion, the positioning of the integrated carrier inside the container portion can also be performed.

Furthermore, in the case where minute quantities of liquid are handled, the carrier is preferably formed as a solid. Moreover, preferably the spacing between the base member and the inner wall of the container is as small as possible. On the other hand, in the case of handling relatively large quantities of liquid, the carrier is preferably formed from a hollow and/or porous member.

According to the first aspect of the invention, since the base member is rolled so that each of the fixed positions of the base member are exposed to the outside, measuring or detection of the labels for the labeled fixed positions can be performed easily and accurately from outside. Consequently, if this integrated carrier is used, then at the time of performing reaction as well as measurement, handling is simplified, and consistent processing can be performed.

A second aspect of the invention is device for containing, reacting and measuring wherein in the first aspect of the invention this has; a transparent container section having a liquid inlet/outlet and which is able to contain a base member with various substances for detection having predetermined chemical structures fixed at respective fixed positions which are arranged in a predetermined condition, and with each of the chemical structures associated with each of the fixed positions, a drawing and discharging section which is able to draw and discharge the liquid into and from the container section via the inlet/outlet, and a measuring device which is able to receive light from the contained base member, external to the container section and in a condition associated with the fixed position.

Since the container section has a liquid inlet/outlet, the base member as well as liquid can be contained in the container section. As a result, reaction between the substance for detection of the base member and the target substance contained in the liquid is possible inside the container section. The container section has a container opening for containing the base member. This container opening may also be used for example for connection to the drawing and discharging section.

Here the base member need not necessarily be a long and slender shape. Moreover, a long and slender base member which is rolled around the integrated carrier is also possible. Furthermore, this may be for example a planar DNA chip. "Predetermined condition" is the condition where each of the fixed positions are exposed to the outside. For example, in the case where the base member is long and slender, this is the condition where each fixed position is arranged in a line along the length of the base member, while in the case where the base member is planar, this is the condition where each fixed position is arranged in matrix form.

Furthermore, the shape or size of the container section may be made a shape or size close to the shape or size of the base member (or the integrated carrier), based on the shape or size of the base member (or integrated carrier), so that the space between the container inner wall and the base member is made narrow, enabling small quantities of liquid to be handled.

According to the second aspect of the invention, reaction or washing can be performed with the same or a different liquid by drawing or discharging the necessary liquid into or from the container section with the base member contained in the container section, and in this condition measurement can also be performed. Consequently, processes such as reaction, measurement and the like can be performed efficiently and consistently, by a quick and a simple operation. Furthermore, since the various processes can be performed with the base member contained in the container section, cross-contamination is prevented so that reliability is high. Moreover, by determining the shape or size of the container section based on the shape or size of the base member, processing can also be performed with minute quantities of liquid.

A third aspect of the invention is a device for containing, reacting and measuring, wherein in the second aspect of the invention, the measuring device has a light receiving section for receiving light from the base member, and a scanning section for relatively moving the light receiving section and the container section and scanning each fixed position of the base member. The scanning section may move the light receiving section, or may move the container section.

According to the third aspect of the invention, by scanning the base member, light from the base member can be received without leakage, and hence reliability of the measurement results is high.

A fourth aspect of the invention is a device for containing, reacting and measuring wherein in the second aspect of the invention, the container section is removably mounted on a nozzle section provided in the drawing and discharging section. According to the fourth aspect of the invention, since the container section for contacting the liquid with the base member is removably mounted, then by replacing container sections, cross-contamination can be reliably prevented. Furthermore, by providing a magnetic force device external to the container section, or by replacing the container section with a pipette section provided with a magnetic force device which can perform separation by attaching magnetic particles to the inner wall, then this can be used in common with a device which uses magnetic particles, and hence many kinds of processing can be performed even more efficiently and consistently.

A fifth aspect of the invention is a device for containing, reacting and measuring wherein in the second aspect of the invention, this further has a moving section which is capable of relatively moving the inlet/outlet and a processing area where externally provided containers or the like are mounted. According to the fifth aspect of the invention, by providing the moving section which relatively moves the inlet/outlet of the container section and the processing area, processing can be automatically and consistently performed by moving the base member with the base member contained in the container section.

A sixth aspect of the invention is a device for containing, reacting and measuring wherein in the second aspect of the invention, this further has an identification section for performing identification of the target substance based on an identification pattern obtained by scanning with the measuring device an area containing all fixed positions of the base member which have been formed by combining labeled target substances with substances for detection. According to the sixth aspect of the invention, an effect the same as for the third aspect of the invention is demonstrated.

A seventh aspect of the invention is a device for containing, reacting and measuring wherein in the second aspect of the invention, the base member is formed in a long and slender shape such as a filament shape, a braid shape, or a tape shape, and the substances for detection are lined up and fixed along a longitudinal direction thereof, and in the case where the base member is contained in a linearly extended condition, the container section is a slender tube, and the base member is contained with the longitudinal direction thereof along the axial direction of the slender tube, and the size and shape of the slender tube is determined based on the size and shape of the base member, and the measuring device measures by scanning along the axial direction of the slender tube. According to the seventh embodiment, since the base member is contained in an extended condition, specifying of each fixed position is simple and accurate.

An eighth aspect of the invention is a device for containing, reacting and measuring wherein in the second aspect of the invention, the base member is formed in a long and slender shape such as a filament shape, a braid shape, or a tape shape, with various substances for detection having predetermined chemical structures lined up and fixed along the longitudinal direction, with each chemical structure associated with the fixed positions thereof, and in the case where the base member forms an integrated carrier rolled on the surface of the carrier with the respective fixed positions exposed outward, the container section comprises a large diameter section for containing the integrated carrier and a small diameter section having an inlet/outlet at a tip end and capable of insertion into an external container, and the drawing and discharging section draws and discharges the liquid into and from the large diameter section via the inlet/outlet, and the size and shape of the container section is determined based on the size and shape of the integrated carrier, and the measuring device receives light from the base member external to the large diameter section. According to the eighth aspect of the invention, by determining the size and shape of the container section based on the size and shape of the integrated carrier, and making the space between the integrated carrier and the inside wall of the container section narrow, processing such as reaction can be performed even with a small quantity of liquid, thus simplifying handling. Furthermore, according to this aspect of the invention, since the base member is integrated and contained as an integrated carrier, measurement can be performed in relation to numerous fixed positions, and hence analysis of complicated structures can also be efficiently performed.

A ninth aspect of the invention is a device for containing, reacting and measuring wherein in the third aspect of the invention, the light receiving section of the measuring device is provided inside a light shielding box, and the light shielding box has a box body, and a cover provided so as to cover an opening of the box body, and has an opening provided in the cover to allow the container section to pass therethrough in order to insert the container section into the box body, and a closure device which covers the opening to form a closure space with the container section inserted into the box body. As well as the light receiving section, the illumination section may also be provided inside the light shielding box. According to the ninth aspect of the invention, since light reception is performed inside the light shielding box, noise of light from outside is shut off, and light does not leak to the outside. Hence there are no adverse effects on other measurements, enabling measurements of high reliability to be performed, and since a plurality of measurements can be performed concurrently in an integrated condition, the efficiency is even higher.

A tenth aspect of the invention is a device for containing, reacting and measuring wherein in the eighth aspect of the invention, the integrated carrier on which the base member is rolled, is contained in a condition with the rolled base member positioned so as not to come in contact with an internal surface of the container section.

To achieve this, for example, the abovementioned protective section may be provided on the integrated carrier.

According to the tenth aspect of the invention, the base member is positioned so as not to come in contact with the internal surface of the container section. Consequently, sufficient contact is possible between the base member and the liquid, and when discharging liquid, a situation where liquid remains in the space between the base member is prevented. Moreover since the base member is positioned, reliable measurement can be performed.

An eleventh aspect of the invention is a method of containing, reacting and measuring having: a containing step for containing in a transparent container, a base member of a long and slender shape such as a filament, a braid, or tape, with various substances for detection having predetermined chemical structures fixed thereto along a longitudinal direction with each of the chemical structures associated with their fixed positions; a reaction step for drawing a liquid suspending a labeled target substance to inside the container section and immersing the base member in the liquid to react the target substance with the substance for detection; a measurement preparation step for removing the liquid and any target substance which has not contributed to the reaction; and a measurement step for measuring light from the base member contained in the container section. Removal in the measurement preparation step is performed for example by washing using a washing solution. Washing is more effectively performed by repeated drawing and discharging of the washing solution or by agitating. According to the eleventh aspect of the invention, effects the same as those described for the second aspect of the invention are demonstrated.

A twelfth aspect of the invention is a method of containing, reacting and measuring wherein in the eleventh aspect of the invention, the measurement step scans all fixed positions of the base member by relatively moving the container section or a light receiving position. According to the twelfth aspect of the invention, effects the same as those described for the third aspect of the invention are demonstrated.

A thirteenth aspect of the invention is a method of containing, reacting and measuring wherein in the eleventh aspect of the invention, in the measurement preparation step there is included a step for drawing measurement liquid after removing target substances which have not contributed to reaction and liquid suspending these, and the measurement step measures in a condition with the base member immersed in the measurement liquid. Here for the easurement liquid it is preferable to use for example distilled water, or a liquid which has a refractive index close to the refractive index of the material constituting the container section. According to the thirteenth aspect of the invention, instead of removing the target substance which has not contributed to the reaction and the liquid in which this is suspended, the measurement liquid is drawn so as to immerse the base member. Consequently, by filling a liquid having for example a predetermined refractive index close to the refractive index of the material constituting the container section, between the container section and the base member, reflection or refraction or distortion produced at the interface between the container section and air can be prevented, thus giving clarity and enabling accurate measurement to be performed.

A fourteenth aspect of the invention is a method of containing, reacting and measuring wherein in the eleventh aspect of the invention, in the reaction step, the container section is shaken, or drawing and discharging is repeated. According to the fourteenth aspect of the invention, by shaking the container section and repeating the drawing and discharging, the encounter characteristic between the target substance suspended in the liquid and the substance for detection of the base member can be increased, and reaction promoted.

BEST MODE FOR CARRYING OUT THE INVENTION

A description is given of a minute object identification device and a minute object identification method according to embodiments of the present invention, based on the drawings. The description of the embodiments is not to be interpreted as limiting the present invention unless particularly specified.

Figure 1:
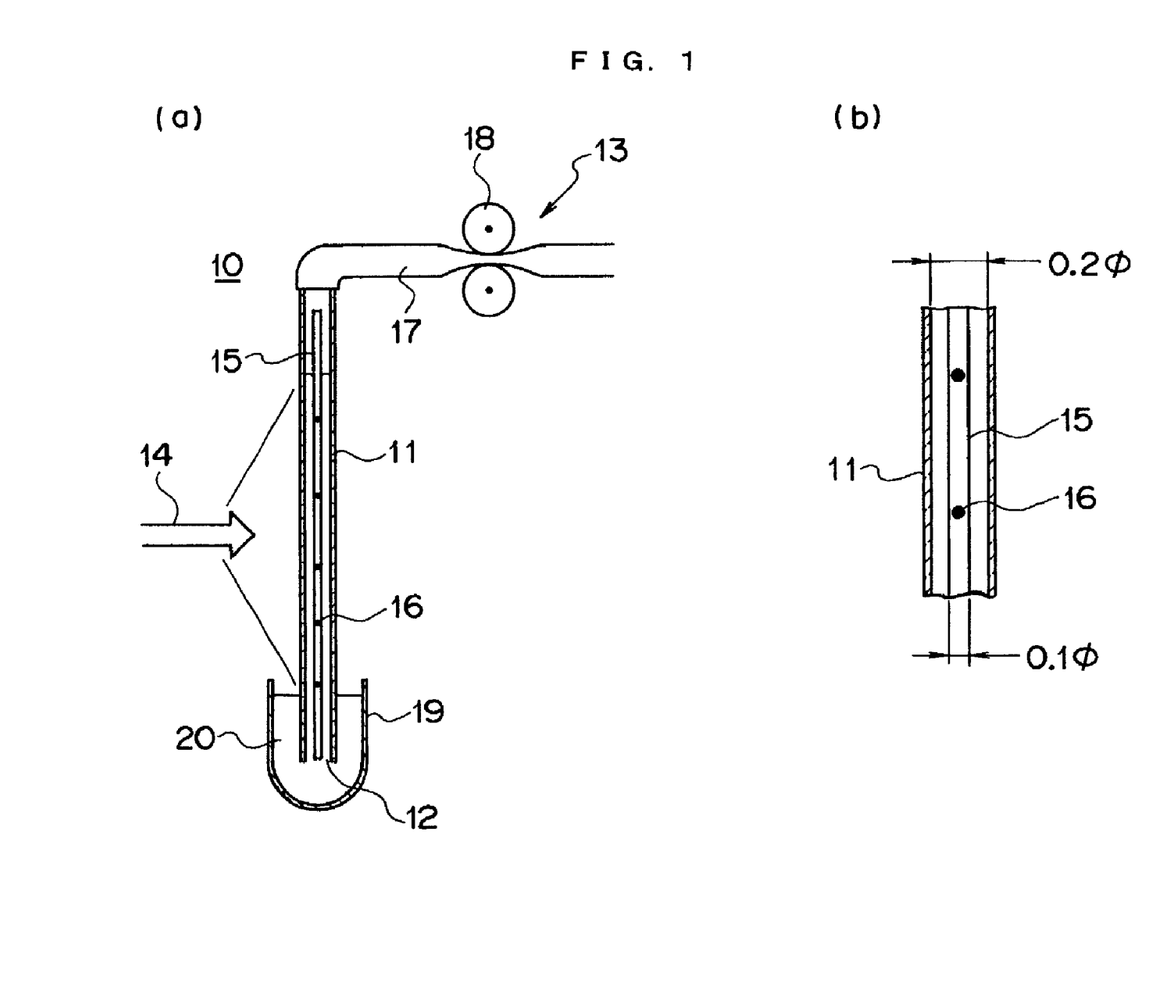
FIG. 1 is a schematic diagram of a device for containing, reacting and measuring according to a first embodiment of the present invention.

FIG. 1(a) schematically shows a device for containing, reacting and measuring 10 according to a first embodiment.

The device for containing, reacting and measuring 10 according to this embodiment has a transparent slender tube 11 serving as the container section and having a liquid inlet 12, a pump 13 connected to the slender tube 11 and serving as a drawing and discharging section for drawing and discharging liquid into and from the slender tube 11, and a measuring device 14. Inside the slender tube 11 it is possible to contain a liquid, and a base member 15 immersed in the liquid.

The base member 15 is formed in a long and slender shape, and detection substances such as for example oligonucleotides having already known various base sequences are arranged so as to be lined up along the longitudinal direction thereof. The base member 15 is contained inside the slender tube 11 in an extended and secured condition so as to adhere to the slender tube 11. Here, reference symbol 16 shows where labeled target substances bond to the detection substance to thereby label fixed positions thereof. By analyzing these labeled fixed positions, the unknown chemical structure of the target substance can be determined.

The pump 13 has a tube 17 made from a resilient body and communicated with the slender tube 11, a pressing section 18 for pressing and contracting the tube 17, and a switching valve (not shown in the figure). The pump 13 draws and discharges into and from the slender tube 11, liquid 20 contained in a container 19 provided external to the device for containing, reacting and measuring 10. In the liquid 20 is suspended a target substance which has been labeled by a fluorescent substance or the like (not shown in the figure).

The measuring device 14 is a device for shining an excitation light beam for exciting the fluorescent substance, and receiving the produced fluorescence. A scanning section (not shown in the figure) which is moved for scanning, is provided along the slender tube 11.

The shape and size of the slender tube 11 is determined based on the shape and size of the base member 15, and is preferably a size and shape such that the base member 15 can be easily contained inside the slender tube 11 with a margin, and so that a gap produced between the inner wall of the slender tube 11 and the surface of the base member 15 is small to the extent that the base member 15 is easily wetted with a small amount of liquid. As shown in FIG. 1(*b*), in order to satisfy this condition, the size of the diameter of the slender tube 11 is suitably approximately two times the size of the width or the diameter of the base member 15, and for example in the case where the diameter of the base member 15 is approximately 0.1 mm, then preferably the diameter of the slender tube 11 is for example approximately 0.2 mm.

Figure 2:
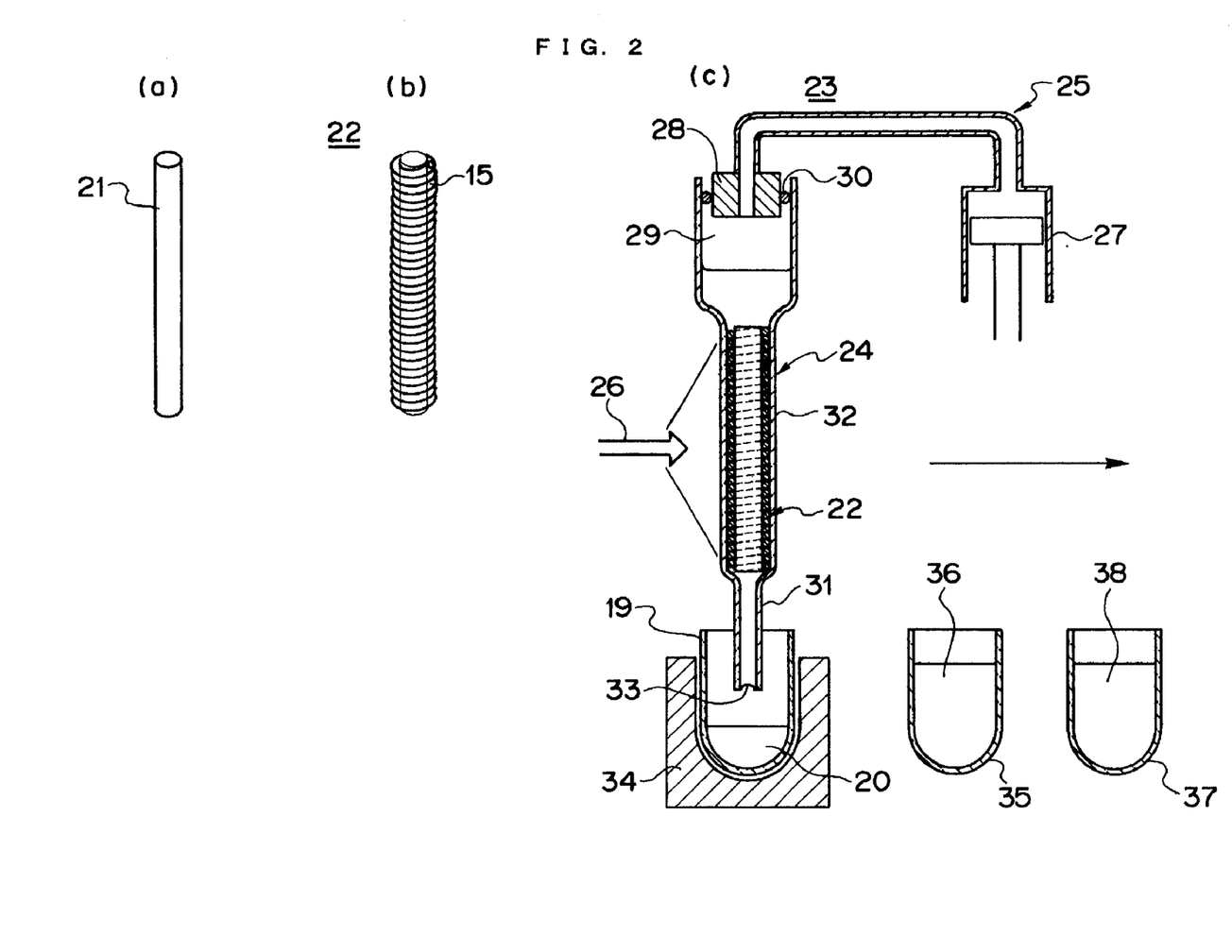
FIG. 2 is a schematic diagram of a device for containing, reacting and measuring according to a second embodiment of the present invention.

Next, FIG. 2 shows a device for containing, reacting and measuring according to a second embodiment.

FIG. 2(*a*) shows a core 21 serving as a rod shape or cylindrical shape carrier for carrying the aforementioned base member 15 rolled around the surface thereof. FIG. 2(*b*) shows an integrated carrier 22 with the beforementioned base member 15 rolled. Here the diameter of the core 21 is for example from approximately 2 to 4 mm, while the thickness of the base member 15 is from approximately 0.05 mm to 0.2 mm, and the length of the base member 15 is for example from approximately 500 mm to 3000 mm. FIG. 2(*c*) illustrates a device for containing, reacting and measuring 23, and a method of containing, reacting and measuring according to the second embodiment.

The device for containing, reacting and measuring 23 has a pipette section 24 serving as the container section, a drawing and discharging section 25 for drawing and discharging into and from the pipette section 24, and a measuring device 26 provided external to the pipette section 24. In the drawing and discharging section 25 is provided a cylinder 27, and a nozzle section 28 communicated with the cylinder 27 through a pipe.

The pipette section 24 has a mounting section 29 removably mounted on the nozzle section 28 via an O-ring 30, a small diameter section 31 having a single inlet/outlet 33 at a tip end, and which is insertable into a container 19 external to the device for containing, reacting and measuring 23, and a large diameter section 32 provided between the small diameter section 31 and the mounting section 29 and having a diameter larger than that of the small diameter section 31 for containing the integrated carrier 22. The opening of the mounting section 29 constitutes a container opening for insertion and accommodation of the integrated carrier 22.

The shape and size of the large diameter section 32 is determined by the shape and size of the integrated carrier 22. The size and shape of the large diameter section 32 is a size where the integrated carrier 22 can be easily contained inside the large diameter section 32 with a margin, and is preferably a size and shape so that a gap produced between the inner wall of the large diameter section 32 and the surface of the base member 15 of the integrated carrier 22 is small to the extent that the base member 15 is easily wetted with a small amount of liquid but does not adhere to the inner wall of the large diameter section 32. Here the amount of liquid is for example approximately 100 m liters.

The drawing and discharging section 25 is for drawing and discharging the liquid 20 into and from the large diameter section 32 via the inlet/outlet 33. Furthermore, with this embodiment, while not shown in the figure, this has a moving mechanism capable of relatively moving the inlet/outlet 33 between externally provided containers 19, 35 and 37.

Moreover, a measuring device 26 is a device which uses for example an optical fiber for irradiating excitation light and receiving the fluorescent, being a movable device which can be scanned in the vertical direction external to the large diameter section 32 of the pipette section 24, and rotated through 360 degrees around the large diameter section 32.

In the device for containing, reacting and measuring 23 according to this embodiment, the pipette section 24 is removably mounted on the nozzle section 28. Consequently, as well as the case of replacing the pipette section with another pipette section of the same construction which is mountable on the nozzle section 28, a pipette with a magnetic force device provided on the outside to thereby exert a magnetic field so that magnetic particles are adhered to the inner wall and can thus be separated, may also be removeably mounted.

Since by so doing, the magnetic particles can be separated, it is possible to consistently perform processing for an even wider range also including for example extraction and separation of genetic material. Consequently, according to this embodiment, by using in common the same drawing and discharging section, various types of processing using magnetic particles, and various types of processing using base members can be consistently and automatically performed.

Next is a description based on FIG. 2, of a method for determining base sequences for analysis of the target substance, using the device for containing, reacting and measuring 23 according to this embodiment.

In FIG. 2(*c*), at first in a step S1, a liquid 20 in which is previously suspended a target substance comprising a DNA fragment for which an unknown base sequence is to be determined and which has been has been labeled with fluorescence, is placed in the container 19.

Furthermore, an integrated carrier 22 with the base member 15 with various already known oligonucleotides with their base sequences and each of their fixed positions associated, rolled around the core 21, is contained inside the large diameter section 32 of the pipette section 24 serving as the container section, and after this the pipette section 24 is mounted on the nozzle section 28.

In step S1, a probe solution with a predetermined reagent mixed in a liquid in which is suspended the target substance labeled with a fluorescent substance or the like, is pre-heated for a few minutes at approximately 95° C. in a constant temperature tank 34 provided with a Peltier element. Then the current direction is changed to thereby cool the solution to for example, a normal temperature or, if necessary, a temperature different from the normal temperature, to adjust the solution to an easily hybridized form. In determining the unknown base sequence of the DNA fragment, needless to say as a pre-requisite, in addition to the hybridization process, a process for denaturation of the DNA fragment is necessary.

In step S2, the small diameter section 31 of the pipette section 24 is moved to the container 19 and inserted therein. The container 19 is held in the constant temperature tank 34 at normal temperature, or if required at a temperature different from the normal temperature, and incubation and reaction is performed over a few minutes to a few hours.

In step S3, after completion of reaction, the small diameter section 31 of the pipette section 24 is moved and inserted into the container 35 which contains a first cleaning solution 36 at room temperature, and this is then shaken and washed so that the excess probe solution in which is suspended the target substance and the like is removed.

In step S4, after the first washing, the small diameter section 31 of the pipette section 24 is moved and inserted into the container 37 which contains unused second cleaning solution 38, and this is again shaken and washed, and the remaining probe solution is removed.

In step S5, the measuring device 26 measures from outside of the integrated carrier for which washing is completed, by scanning the perimeter of the large diameter section 32 vertically and through 360 degrees therearound with the scanning section.

Figure 3:
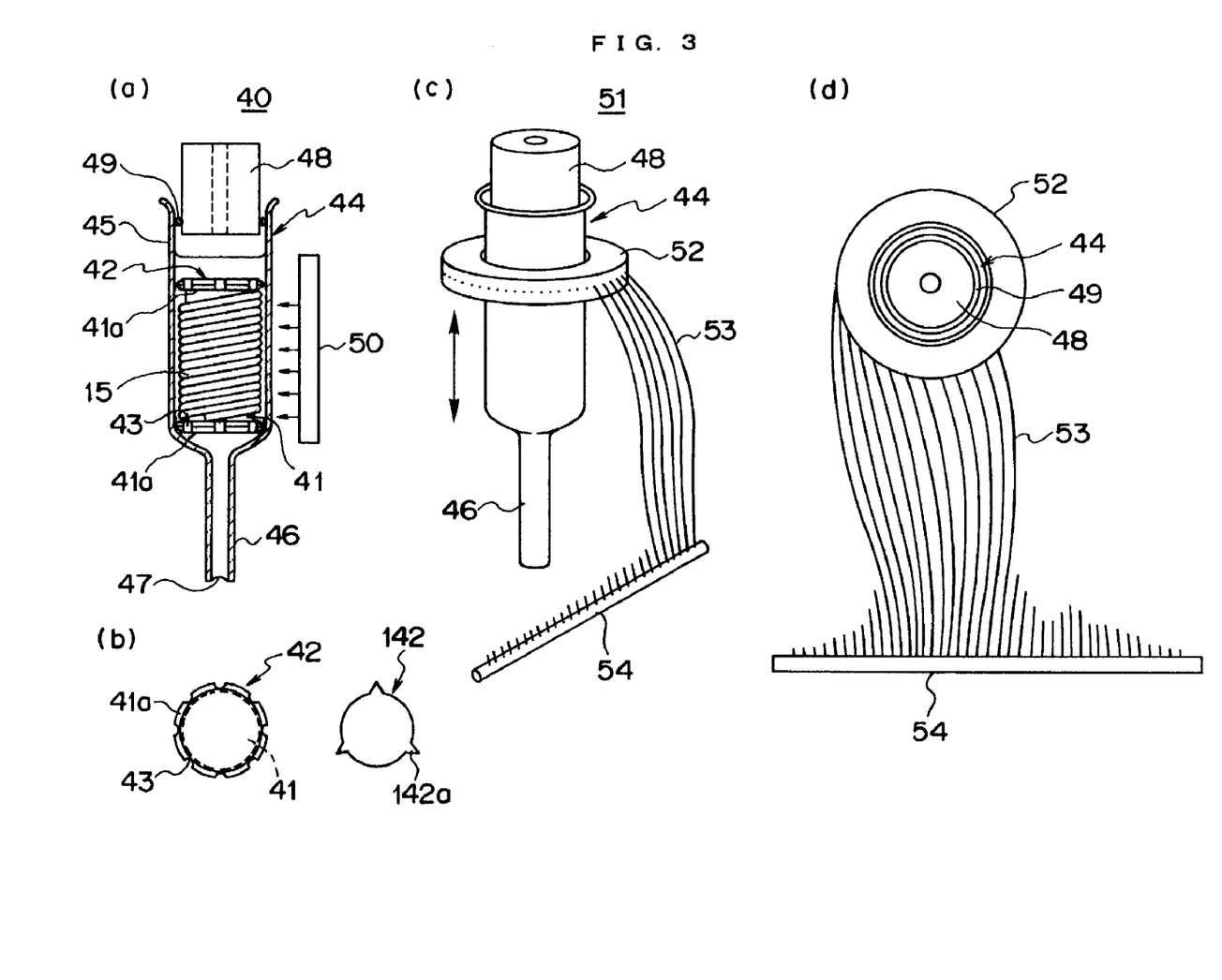
FIG. 3 is a schematic diagram of a device for containing, reacting and measuring according to a third and fourth embodiment of the present invention.

Next, is a description of a device for containing, reacting and measuring 40 according to a third embodiment, based on FIG. 3.

FIG. 3(a) schematically shows the device for containing, reacting and measuring 40 according to the third embodiment. This device for containing, reacting and measuring 40 uses another integrated carrier 42. The integrated carrier 42, as shown in FIG. 3(a) has the base member 15 rolled around a core 41 as the carrier.

As shown in FIG. 3(b), at opposite rims of the core 41 are respectively provided annular protruding portions 41a serving as the protective portions. By means of these protective portions, the base member 15 is bound so as not to come off from the core 41 being the carrier, and contact between an inner wall of a pipette section 44 serving as a later mentioned container section and the base member 15 is prevented, so that the liquid passing the surface of the base member 15 flows smoothly, and the integrated carrier 42 is positioned inside the container section, thus enabling reliable measurement. Consequently, the core 41 is formed in an overall spool shape.

On these annular protruding portions 41a are provided a plurality of cut out portions 43 so that the liquid can pass therethrough, and the contact portions at the tip of the annular protruding portion 41a which contact with the inner wall are formed in a wedge shape so that the contact area with the inner wall is minimal. As a result, liquid residue is prevented, and the process can be smoothly performed. The height of the annular protruding portions 41a is made a height exceeding the thickness of the rolled base member 15, to thereby prevent the base member 15 from touching or adhering to the inner wall.

Furthermore, instead of the annular protruding portions 41a, protective portions 142 as shown in FIG. 3(b) may be provided. With these protective portions 142, a plurality of radially protruding portions 142a are provided, and the height of these protruding portions 142a is set so as to exceed the thickness of the base member 15.

The device for containing, reacting and measuring 40 which uses the integrated carrier 42, has a pipette section 44 serving as the container section, a drawing and discharging section (48) for performing drawing and discharging into and from the pipette section 44, and a linear light receiving and irradiating section 50 provided external to the pipette section 44. Reference symbol 48 denotes a nozzle section provided in the drawing and discharging section (48).

The linear light receiving and irradiating section 50 is attached to a rod shape support member with tip sections of a large number of optical fibers arranged in a line. Each of the fibers is connected to a photodetector and a light source for irradiating excitation light for exciting the fluorescent substances used in the labeling. As a result, the fluorescence excited thereby can be simultaneously received.

Furthermore, the linear light receiving and irradiating section 50 may be such that direct photodetectors are arranged in a line, and there is provided a light source for irradiating excitation light. This linear light receiving and irradiating section 50 is provided so as to be able to be turned through 360 degrees around the periphery of the large diameter section 45 by means of a scanning section (not shown in the figure). Furthermore, the mounting portion containing the pipette section 44 may be provided so as to be able to be rotated through 360 degrees around the axis of the pipette section 44. This linear light receiving and irradiating section 50 corresponds to the measuring device.

The pipette section 44 has a removably mounted large diameter section 45 engaged with the nozzle section 48 via an O-ring 49, and which contains the integrated carrier 42, and a small diameter section 46 with a tip having an inlet/outlet 47, which can be inserted into a container external to the device for containing, reacting and measuring 40. Here the diameter of the large diameter section 45 is for example an inner diameter of approximately 4 mm. The opening of the large diameter section 45 constitutes the container opening for insertion and accommodation of the integrated carrier.

Here the annular protruding portion 41a of the integrated carrier 42 is preferably formed in a size to contact with the inner wall of the large diameter section 45. The outside diameter of the integrated carrier 42 is for example approximately 3.8 mm.

FIG. 3(c) shows a device for containing, reacting and measuring 51 according to a fourth embodiment. This device for containing, reacting and measuring 51 uses an annular light receiving and irradiating section 52 as the measuring device, instead of the linear light receiving and irradiating section 50 formed in the linear shape. To the annular light receiving and irradiating section 52 is fitted an annular support member with tip portions of a large number of optical fibers 53 arranged annularly. These optical fibers 53 irradiate excitation light and at the same time receive fluorescence.

The other ends of the optical fibers 53 are connected to a line sensor 54 comprising photodetectors arranged in a line. Furthermore, the other ends of the optical fibers 53 may be connected to a planar CCD element. Moreover, this annular light receiving and irradiating section 52 is provided so as to be moveable vertically by means of a scanning section (not shown in the figure). Moreover, an equipment part including the pipette section 44 may be provided so as to be moveable vertically by means of the scanning section.

Figure 4:
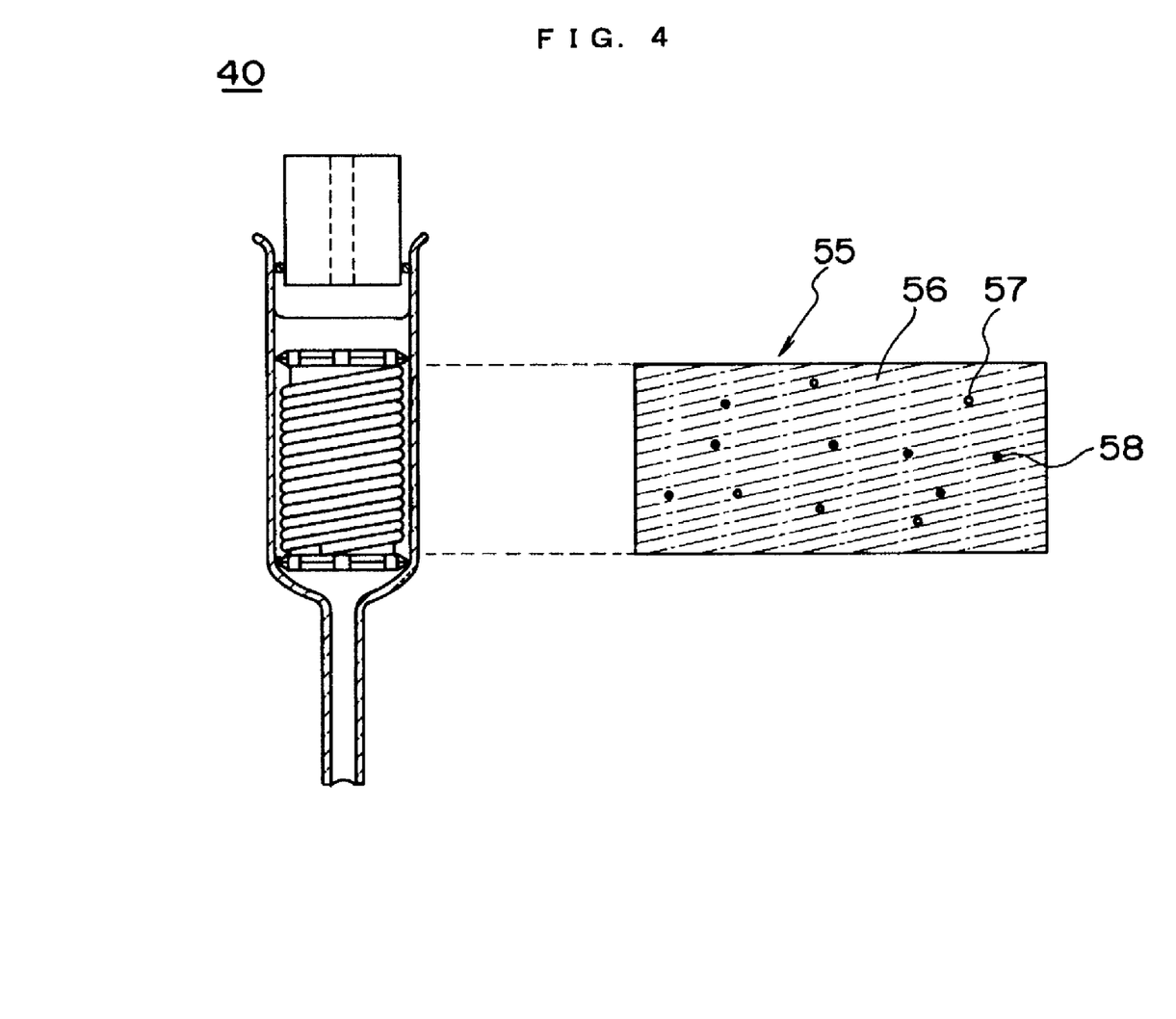
FIG. 4 is a diagram showing an example of an identification pattern of a device for containing, reacting and measuring according to the third and fourth embodiments of the present invention.

FIG. 4 schematically shows one example of a measured identification pattern 55. Here reference symbol 56 denotes positions on an image of the base member 15. Reference symbol 57 denotes reference points which are labeled beforehand so as to become references for specifying fixed positions of the base member 15. Reference symbol 58 shows fixed positions where the labeled target substance has been combined. According to this example, the measurement results for each of the labeled fixed positions may be processed as planar information.

Figure 5:
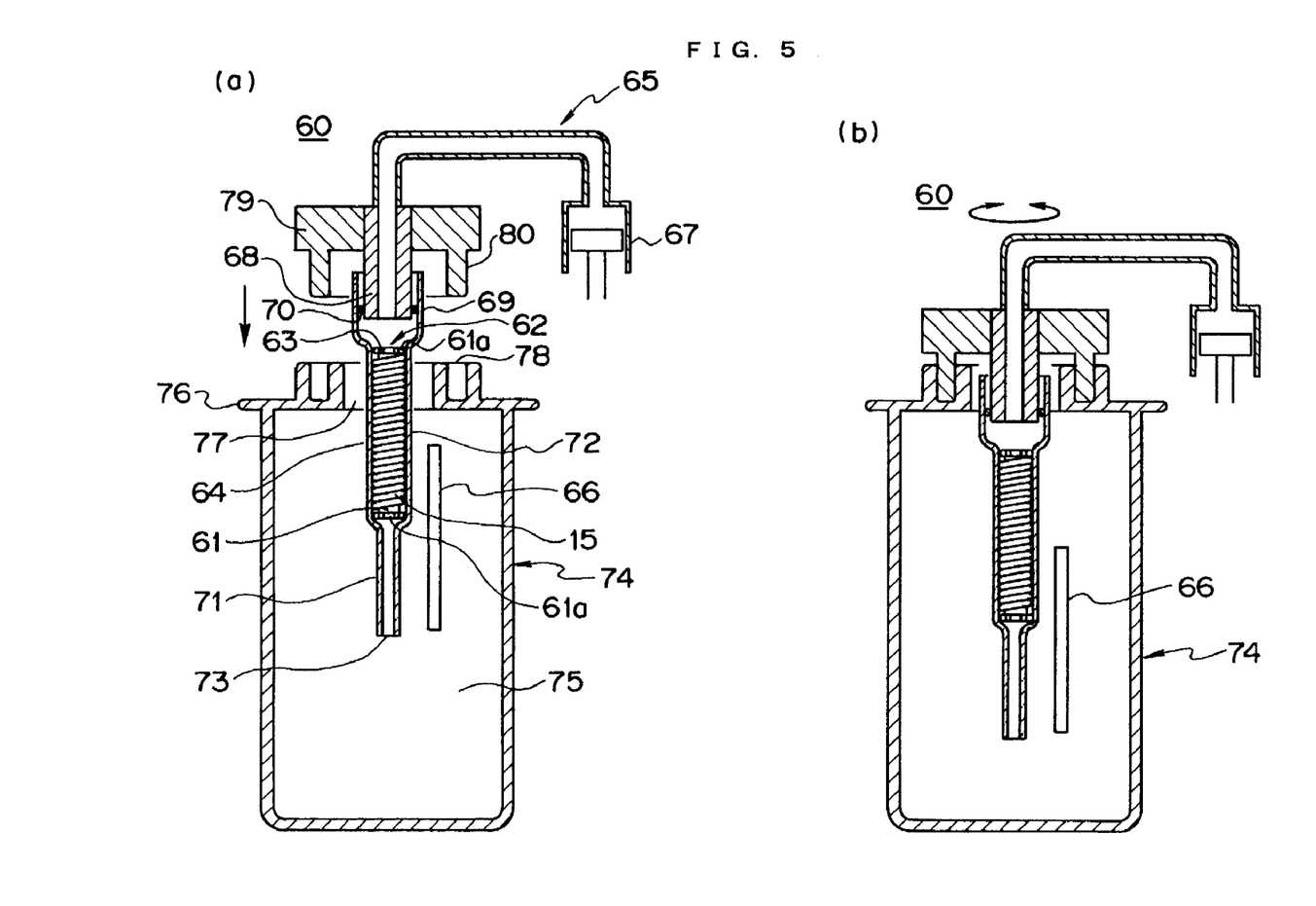
FIG. 5 is a schematic diagram of a device for containing, reacting and measuring according to a fifth embodiment of the present invention.

Next is a description of a device for containing, reacting and measuring 60 according to a fifth embodiment, based on FIG. 5. As schematically shown in FIGS. 5(a) and (b), the device for containing, reacting and measuring 60 according to this embodiment has; a pipette section 64 serving as the container section, a drawing and discharging section 65 for drawing and discharging into and from the pipette section 64, and a measuring device 66 provided external to the pipette section 64. In the drawing and discharging section 65 is provided a cylinder 67, and a nozzle section 68 communicated with the cylinder 67 through a pipe.

The pipette section 64 has a removably mounted mounting section 69 engaged with the nozzle section 68 via an O-ring 70, a small diameter section 71 with a tip having an inlet/outlet 73, and which is insertable into a container external to the device for containing, reacting and measuring 60, and a large diameter section 72 provided between the small diameter section 71 and the mounting section 69 and having a diameter larger than that of the small diameter section 71 for containing an integrated carrier 62.

The integrated carrier 62 is one where the base member 15 is rolled around a core 61. At opposite ends of the core 61 are respectively provided annular protruding portions 61a serving as the protective portions for protecting so that the base member 15 does not to come off from the core 61 and the base member 15 does not contact with the inner wall, and for ensuring smooth flow of the liquid, and for positioning. The core 61 is formed overall in a spool shape, and on these annular protruding portions 61a are provided a plurality of cut out portions 43 so that the liquid can pass therethrough.

Here the annular protruding portions 61a of the integrated carrier 62 are preferably formed in a size so as to contact with the inner wall of the large diameter section 72.

The drawing and discharging section 65 is for drawing and discharging the liquid into and from the large diameter section 72 via the inlet/outlet 73. Furthermore this embodiment, while not shown in the figure, has a moving mechanism which can relatively move the inlet/outlet 73 between various processing areas and processing positions such as externally provided containers, and a later described light shielding box 74.

With this embodiment, the measuring device 66 is provided in the light shielding box 74. The light shielding box 74 is used for shutting off noise of excess light generated from the exterior or from the interior at the time of measuring the fluorescence generated by the integrated carrier 62. The light shielding box 74 has a box body 75 provided with the measuring device 66 and with the pipette section 64 inserted thereinside, and a cover 76 provided on an opening of the box body 75. An aperture 77 is formed in a central portion of the cover 76 for enabling insertion of the pipette section 64. Moreover, around the periphery of the aperture 77 a double annular wall section 78 is provided upwardly protruding so as to form an annular groove therebetween.

On the other hand, an annular cover plate 79 for covering the aperture 77 is provided so as to protrude sideways from the surroundings of the upper portion of the nozzle section 68. On a lower side of the cover plate 79 provided so as to protrude downwards, is an annular protrusion 80 for insertion into the groove formed by the double annular wall 78 to form an enclosed space thereinside. Here the cover plate 79, the double annular wall 78 and the annular protrusion 80 correspond to a closure device.

Furthermore, with the device for containing, reacting and measuring 60 according to this embodiment, there is provided a rotation section (not shown in the figure) serving as the scanning section, which can rotate a part containing the pipette section 64 through 360 degrees in relation to the central axis of the pipette section 64. By rotation by this rotation section, the annular protrusion 80 slides inside the groove formed in the double annular wall section 78. As a result, complete light shielding is achieved, and all of the fixed positions provided on the integrated carrier 62 contained inside the large diameter section 72 can be scanned and the light received without any leakage.

FIG. 5(a) shows the condition where the pipette section 64 is being moved downward by the moving section (not shown in the figure) in order to insert the pipette section 64 inside the light shielding box 74, while FIG. 5(b) shows the condition where insertion of the pipette section 64 into the light shielding box 74 has been completed, and measurement is being performed.

Figure 6:
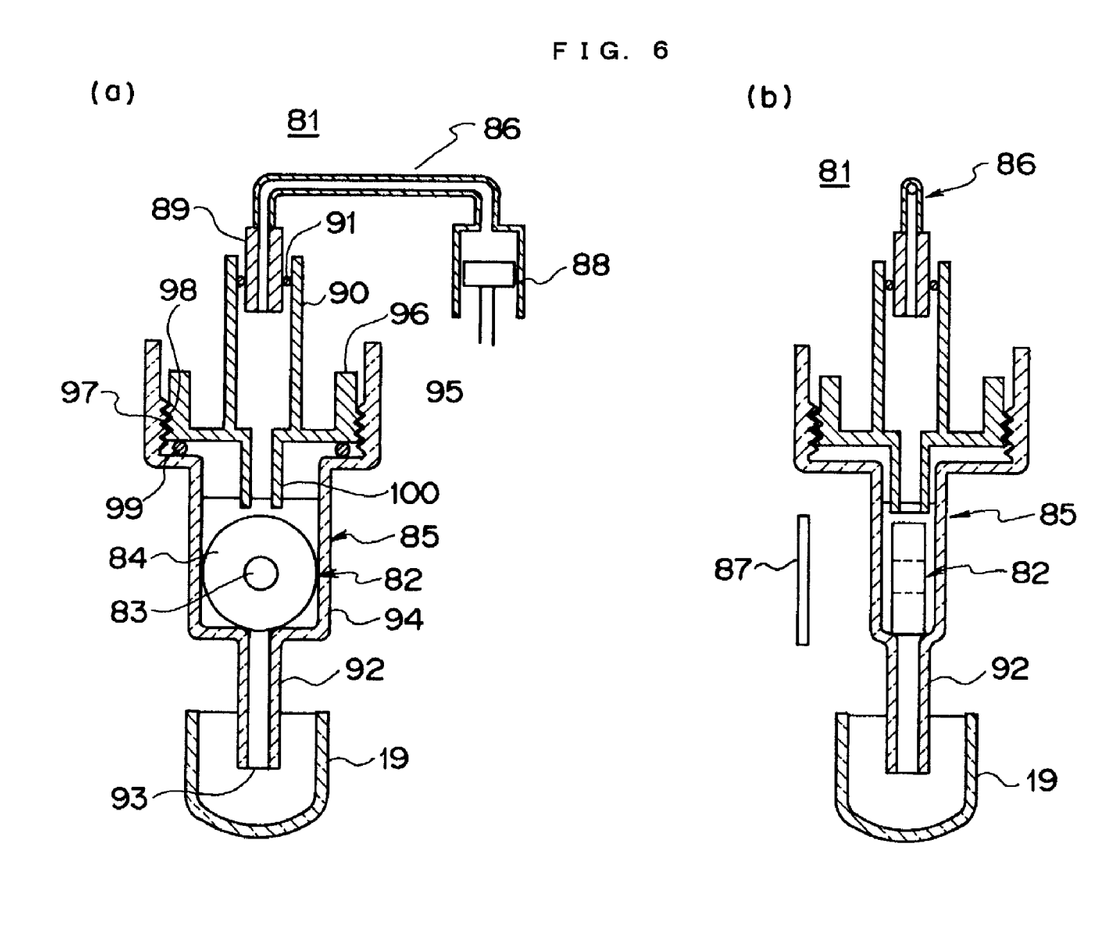
FIG. 6 is a schematic diagram of a device for containing, reacting and measuring according to a sixth embodiment of the present invention.

Next is a description of a device for containing, reacting and measuring 81 according to a sixth embodiment, based on FIG. 6.

The device for containing, reacting and measuring 81 according to this embodiment, as shown in FIGS. 6(a) and (b) has; a pipette section 85 serving as the container section, a drawing and discharging section 86 for drawing and discharging into and from the pipette section 85, and a measuring device 87 provided external to the pipette section 85. In the drawing and discharging section 86 is provided a cylinder 88, and a nozzle section 89 communicated with the cylinder 88 through a pipe.

The pipette section 85 has a removably mounted mounting section 90 engaged with the nozzle section 89 via an O-ring 91, a small diameter section 92 with a tip having an inlet/outlet 93, and which is insertable in a container 19 external to the device for containing, reacting and measuring 81, and a large diameter section 94 provided between the small diameter section 92 and the mounting section 90 and having a diameter larger than that of the small diameter section 92 for containing an integrated carrier 82. The opening of the large diameter section 94 constitutes the container opening for insertion and accommodation of the integrated carrier.

The integrated carrier 82 has a region 84 where this is rolled as a spiral within a plane on the core 83 being the center of the base member 15, and is different from the aforementioned integrated carriers 42 and 62 where the base member 15 is rolled in one layer only in a cylindrical shape.

Furthermore, in the device for containing, reacting and measuring 81 according to this embodiment, a cylindrical external screw section 96 is provided beneath the mounting section 90 with a thread 98 provided on an external surface thereof. On the other hand, a cylindrical recess screw section 95 is provided on an upper portion of the large diameter section 94, with a screw thread 97 provided on an internal surface thereof. Moreover, an O-ring 99 is provided between the external screw section 96 and the recess screw section 95 to give high water tightness.

As a result, with this embodiment, the integrated carrier 82 which has a greater diameter than the mounting section 90 can be easily accommodated by unfastening the external screw section 96 from the recess screw section 95. A pipe 100 of a predetermined length may be provided so as to protrude from the lower side of the external screw section 96 to prevent lifting of the integrated carrier 82, and enable the integrated carrier 82 to be accommodated and fixed in a predetermined position.

Furthermore, instead of the case where, as described above, the large diameter section and the mounting section are provided so as to be able to be opened and closed by means of the screw sections so that the base member (or the DNA chip or the integrated carrier) is provided so as to be able to be accommodated or taken out, after accommodating the base member in the large diameter section, this may be sealed in by welding with ultrasonic welding or the like between the mounting section and the large diameter section. In this case, since from the start the base member is accommodated inside the container section, then the reliable prevention of cross-contamination is possible.

The above described respective embodiments have been described in detail to further explain the present invention, and in no way preclude other embodiments. Consequently the embodiments can be altered provided the gist of the invention is retained. For example, with each of the embodiments, the description was only for the case where oligonucleotides were used as the detection substance. However the invention is not limited to this case, and for example not only other genetic material but also immunity substances, amino acids, proteins, sugars and so forth may be used. Furthermore, in the first embodiment, the description was for the case where a pump was used as the drawing and discharging section. However the invention is not limited to this case, and for example this may comprise a cylinder and piston.

Moreover, in the above description, the case where fluorescence was measured as the measurement device was described. However the case of chemiluminescence, or measurement of electromagnetic waves of various wavelengths is also possible. For example, the case of measuring wavelength ranges of electromagnetic waves of for example infrared rays, ultraviolet rays, X-rays, radio waves and so forth outside of the visual light, as the electromagnetic waves is also possible.

Furthermore, in the above description, only the case where each pipette section or slender tube was one set was described. However the invention is not limited to this case, and for example a case where multiple sets of pipette sections or slender tubes are provided in rows is also possible. As a result, processing can be made even more efficient. Moreover, needless to say, the numerical values used in the above description are only for example, and are not limiting to the invention. Furthermore, the various components constituting the device for containing, reacting and measuring described in the various embodiments may be optionally selected and suitably modified and combined to thereby make up new apparatus for containing, reacting and measuring.

The invention claimed is:

1. A device comprising:
a transparent tubular member having a liquid inlet/outlet and an opening;
a base member contained through the opening and disposed in the transparent tubular member;
a plurality of detection substances fixed to the base member wherein each detection substance comprises a predetermined chemical structure and is fixed to the base member at a predetermined fixed position;
a source of a liquid comprising at least one target substance;
a light shielding box wherein the transparent tubular member is disposed in the light shielding box;
a means connected to the transparent tubular member at the opening for drawing liquid into the transparent tubular member from the source, and discharging the liquid from the transparent tubular member via the inlet/outlet; and
a means positioned outside of the transparent tubular member for identifying the target substance after the target substance has reacted with a corresponding one of the detection substances fixed to the base member, the identifying means comprising:
a means for receiving emissions propagating through the wall of the transparent tubular member and from the predetermined fixed positions.

2. The device of claim 1 further comprising means for effecting relative movement between the receiving means and the tubular member.

3. The device of claim 2 wherein the movement is translational and/or rotational.

4. The device of claim 1
wherein the base member has a longitudinal length, and an unrolled configuration in which:
the detection substances are arranged in a predetermined order along the longitudinal length of the base member; and
each pair of adjacent detection substances are spaced at a predetermined longitudinal spacing along the longitudinal length of the base member.

5. The device of claim 1 further comprising a core wherein the base member is spirally wound around the core.

6. The device of claim 1 wherein the reactions at the corresponding predetermined fixed positions result in an identification pattern.

7. The device of claim 1 wherein the emissions are in the form of fluorescence.

8. The device of claim 1 wherein the emissions are in the form of chemiluminescence.

9. The device of claim 1 wherein the emissions are in the form of electromagnetic waves.

10. The device of claim 1 wherein the receiving means is disposed in the light shielding box.

11. The device of claim 1 further comprising a light source for irradiating excitation light through the wall of the tubular member.

12. The device of claim 11 wherein the receiving means comprises at least one photodetector.

13. The device of claim 12 further comprising at least one optical fiber connected to the light source and the photodetector.

14. The device of claim 13 wherein the irradiating and the receiving occur simultaneously.

15. The device of claim 13 further comprising:
at least one other optical fiber;
wherein the receiving means further comprises at least one other photodetector; and
wherein the one other optical fiber is connected to the light source and the one other photodetector.

16. The device of claim 15 further comprising a rod member spaced from the tubular member in a parallel relation wherein a tip section of each optical fiber is connected to the rod member.

17. The device of claim 15 further comprising an annular member surrounding the tubular member wherein a tip section of each optical fiber is connected to the annular member.

18. A device comprising:
a light shielding box;
a transparent tubular member disposed in the light shielding box;
a base member disposed in the transparent tubular member;
a plurality of detection substances fixed to the base member wherein each detection substance comprises a predetermined chemical structure and is fixed to the base member at a predetermined fixed position;
a means connected to the transparent tubular member for drawing liquid into the transparent tubular member and discharging the liquid from the transparent tubular member wherein at least one target substance is suspended in the liquid and reacts with the detection substances at the corresponding predetermined fixed positions; and a means positioned outside of the transparent tubular member for identifying the target substance after the target substance has reacted with the detection substances, the identifying means comprising:
  a means for irradiating excitation light through the wall of the transparent tubular member; and
  a means for receiving emissions propagating through the wall of the transparent tubular member and from the predetermined fixed positions in response to the excitation light.

19. The device of claim 18 wherein the receiving means is disposed in the light shielding box.

20. The device of claim 1 further comprising a cylindrical structure having a longitudinal axis;
  wherein the base member has:
    a rolled configuration in which:
      the base member is rolled around the cylindrical structure to define a plurality of circumferentially-extending rolls;
      each pair of adjacent rolls in the plurality of circumferentially-extending rolls are spaced at a predetermined axial spacing along the longitudinal axis of the cylindrical structure; and
  wherein the base member is disposed in the transparent tubular member such that:
    each detection substance is exposed outwards at the corresponding predetermined fixed position relative to the outer surface of the cylindrical structure; and
    each predetermined fixed position is defined by:
      the predetermined order along the longitudinal length of the base member,
      the predetermined longitudinal spacings along the longitudinal length of the base member, and
      the predetermined axial spacings along the longitudinal axis of the cylindrical structure.

* * * * *

UNITED STATES PATENT AND TRADEMARK OFFICE
CERTIFICATE OF CORRECTION

PATENT NO.       : 7,157,047 B2                                          Page 1 of 1
APPLICATION NO.  : 09/909186
DATED            : January 2, 2007
INVENTOR(S)      : Hideji Tajima It is certified that error appears in the above-identified patent and that said Letters Patent is hereby corrected as shown below:

Title Page, (75) Inventor, residence "Inagi (JP)" should read --Toyko (JP)--

Signed and Sealed this

Twenty-seventh Day of November, 2007

JON W. DUDAS
*Director of the United States Patent and Trademark Office*